US010335184B2

(12) United States Patent
Locke (10) Patent No.: US 10,335,184 B2
(45) Date of Patent: Jul. 2, 2019

(54) NEGATIVE PRESSURE TISSUE DEBRIDEMENT DEVICES, SYSTEMS, AND METHODS

(71) Applicant: KCI Licensing, Inc., San Antonio, TX (US)

(72) Inventor: Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 209 days.

(21) Appl. No.: 14/689,842

(22) Filed: Apr. 17, 2015

(65) Prior Publication Data

US 2015/0351785 A1 Dec. 10, 2015

Related U.S. Application Data

(60) Provisional application No. 62/007,790, filed on Jun. 4, 2014, provisional application No. 62/007,775, filed on Jun. 4, 2014.

(51) Int. Cl.
*A61B 17/3205* (2006.01)
*A61B 17/54* (2006.01)
(Continued)

(52) U.S. Cl.
CPC .......... *A61B 17/3205* (2013.01); *A61B 17/54* (2013.01); *A61B 2017/00544* (2013.01);
(Continued)

(58) Field of Classification Search
CPC ............ A45D 29/14; A45D 2200/1054; A61H 7/004; A47L 5/26; A61B 17/54;
(Continued)

(56) References Cited

U.S. PATENT DOCUMENTS 500,415 A * 6/1893 Neal ...................... A47L 9/0416
15/23
1,355,846 A 10/1920 Rannells
(Continued)

FOREIGN PATENT DOCUMENTS

AU 550575 B2 3/1986
AU 745271 B2 3/2002
(Continued)

OTHER PUBLICATIONS

European Search Report for corresponding Application No. 15170632.2 dated Oct. 30, 2015.
(Continued)

*Primary Examiner* — Thomas M Mcevoy (57) ABSTRACT

In some embodiments, a debridement tool may include a housing, a reduced-pressure lumen, a debridement head, an impeller, and a drive system. The debridement head may be moveable relative to the housing. The impeller may be positioned in fluid communication with the reduced-pressure lumen and be moveable relative to the housing by operation of reduced pressure being applied to the impeller. The drive system may be coupled between the impeller and the debridement head and be configured to impart movement from the impeller to the debridement head.

24 Claims, 4 Drawing Sheets

(51) Int. Cl.
    *A61B 17/00* (2006.01)
    *A61B 17/32* (2006.01)
(52) U.S. Cl.
    CPC .............. *A61B 2017/00553* (2013.01); *A61B 2017/00561* (2013.01); *A61B 2017/00761* (2013.01); *A61B 2017/320004* (2013.01); *A61B 2017/320012* (2013.01); *A61B 2217/005* (2013.01)
(58) Field of Classification Search
    CPC .... A61B 2017/320012; A61B 17/3205; A61B 2017/00544; A61B 2017/00561; A61B 2017/00553; A61B 2017/00761; A61B 2017/320004; A61B 2017/320008; A46B 13/001
    See application file for complete search history.

(56) References Cited

U.S. PATENT DOCUMENTS

| | | |
|---|---|---|
| 2,049,874 A | 8/1936 | Sherk |
| 2,547,758 A | 4/1951 | Kelling |
| 2,632,443 A | 3/1953 | Lesher |
| 2,682,873 A | 7/1954 | Evans et al. |
| 2,812,155 A * | 11/1957 | Woodruff .................. A47L 4/00 15/387 |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,294,595 A * | 10/1981 | Bowerman ................ A47L 9/19 15/339 |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,388,302 A * | 2/1995 | Sundaram ................ A47L 9/22 15/344 |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,185,781 B1 | 2/2001 | Miller et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,477,735 B2 * | 11/2002 | Worwag ................ A47L 9/0416 15/387 |
| 6,488,643 B1 | 12/2002 | Tumey et al. |
| 6,493,568 B1 | 12/2002 | Bell et al. |
| 6,500,183 B1 | 12/2002 | Waldron |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0107527 A1* | 8/2002 | Burres ................... A45D 29/14 606/131 |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0010268 A1 | 1/2004 | Gabehart |
| 2005/0142093 A1* | 6/2005 | Skover ................... A61Q 19/08 424/70.14 |
| 2011/0028993 A1* | 2/2011 | Menke ................... A61B 17/54 606/131 |
| 2013/0139350 A1* | 6/2013 | Conrad ................ A47L 9/0416 15/387 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 202011104490 U1 | 11/2011 |
| EP | 0100148 A1 | 2/1984 |

(56) References Cited

FOREIGN PATENT DOCUMENTS

| | | |
|---|---|---|
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 1815942 A1 | 8/2007 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2004002339 A1 | 1/2004 |
| WO | 2007080020 A1 | 7/2007 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, (56) References Cited

OTHER PUBLICATIONS edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

NEGATIVE PRESSURE TISSUE DEBRIDEMENT DEVICES, SYSTEMS, AND METHODS

CROSS-REFERENCE TO RELATED APPLICATIONS

This application claims priority to U.S. Provisional Patent Application Ser. No. 62/007,790, filed Jun. 4, 2014, and U.S. Provisional Patent Application Ser. No. 62/007,775, filed Jun. 4, 2014. The entire contents of each of the applications set forth above are expressly incorporated herein by reference.

FIELD

This disclosure relates generally to medical treatment systems and, more particularly, but not by way of limitation, to debridement devices, systems, and methods suitable for debriding a tissue site.

BACKGROUND

Debridement may refer to a process for removing dead, damaged, or infected tissue from a tissue site for improving the healing potential of healthy tissue remaining at the tissue site. Several factors may make proper debridement difficult, such as challenging wound locations, immobile patients, and environmental constraints. Further, training in the proper use of debridement tools may be time consuming, thereby presenting additional challenges. For example, the action of cutting or abrading away dislodged eschar or necrotic tissue may be difficult to perform with conventional debridement tools, which may be capable of causing damage to healthy tissue and extensive bleeding. Thus, specialized training may be required in proper debridement techniques for performing thorough debridement of a tissue site while minimizing damage to healthy tissue. Therefore, improvements to debridement tools, systems, and methods that may reduce the amount of training and risk of damage to healthy tissue associated with conventional methodologies may be desirable.

SUMMARY

Shortcomings with certain aspects of tissue debridement tools, systems, and methods are addressed as shown and described in a variety of illustrative, non-limiting embodiments herein.

In some embodiments, a debridement tool for debriding tissue from a tissue site may include a housing, a reduced-pressure lumen, a debridement head, an impeller, and a drive system. The housing may have an interior space. The reduced-pressure lumen may be adapted to communicate reduced pressure. The debridement head may be moveable relative to the housing. The impeller may be moveable relative to the housing and positioned in fluid communication with the reduced-pressure lumen. The drive system may be coupled between the impeller and the debridement head. Further, the drive system may be configured to impart movement from the impeller to the debridement head.

In other embodiments, a debridement tool for debriding tissue from a tissue site may include a housing, a reduced-pressure lumen, a debridement head, an impeller, and a drive system. The housing may include an interior space and a working surface. The working surface may be adapted to face the tissue site, and a working surface port may be disposed through the working surface. The reduced-pressure lumen may be adapted to communicate reduced pressure and may be in fluid communication with the working surface through the working surface port. The debridement head may be moveable relative to the housing. The impeller may be moveable relative to the housing and positioned in fluid communication with the reduced-pressure lumen. The drive system may be coupled between the impeller and the debridement head. Further, the drive system may be configured to impart movement from the impeller to the debridement head.

In other embodiments, a debridement tool for debriding tissue from a tissue site may include a housing, a handle, a reduced-pressure lumen, a feedback pressure lumen, a debridement head, an impeller, and a drive system. The housing may include an interior space and a working surface. The working surface may be adapted to face a tissue site and may have a working surface port disposed through the working surface. Further, the working surface may be in fluid communication with the interior space through the working surface port. The handle may be coupled to the housing. The reduced-pressure lumen may be in fluid communication with the working surface port and may be adapted to communicate reduced pressure. Further, the reduced-pressure lumen may be in fluid communication with the interior space through the handle. The feedback pressure lumen may be in fluid communication with the interior space and may be adapted to communicate reduced pressure. Further, the feedback pressure lumen may be in fluid communication with the interior space through the handle. The debridement head may be moveable relative to the housing and may have an exterior surface rotatable about a debridement head axis. The exterior surface of the debridement head may comprise an abrasive portion. Further, the debridement head may be positioned within the interior space, and at least a portion of the exterior surface of the debridement head may be adapted to protrude through the working surface port. The impeller may be moveable relative to the housing and may be positioned in fluid communication with the reduced-pressure lumen. The impeller may include a plurality of impeller vanes rotatable about an impeller axis and may be adapted to rotate by operation of reduced pressure being applied to the impeller vanes. Further, the impeller may be positioned in fluid communication with the interior space. The drive system may be coupled between the impeller and the debridement head. The drive system may include an impeller pulley, a debridement head pulley, and a drive belt. The impeller pulley may be coupled to the impeller and rotatable about the impeller axis. The debridement head pulley may be coupled to the debridement head and rotatable about the debridement head axis. The drive belt may be positioned about the impeller pulley and the debridement head pulley such that the drive system may be configured to impart movement from the impeller to the debridement head.

In some embodiments, system for debriding tissue from a tissue site may include a debridement tool and a reduced-pressure source. The debridement tool may include a housing, a reduced-pressure lumen, a debridement head, an impeller, and a drive system. The housing may have an interior space. The reduced-pressure lumen may be adapted to communicate reduced pressure. The debridement head may be moveable relative to the housing. The impeller may be moveable relative to the housing and positioned in fluid communication with the reduced-pressure lumen. The drive system may be coupled between the impeller and the debridement head. Further, the drive system may be configured to impart movement from the impeller to the debridement head. The reduced-pressure source may be in fluid communication with the impeller through the reduced-pressure lumen.

In some embodiments, a method for debriding tissue at a tissue site may include providing a debridement tool. The debridement tool may include a housing, a debridement head, an impeller, and a drive system. The housing may include a working surface, and the debridement head may be moveable relative to the working surface. The drive system may be coupled between the impeller and the debridement head. The method may further include communicating reduced pressure to the working surface, and communicating reduced pressure to the impeller. The impeller may be configured to rotate by operation of reduced pressure being applied thereto. The method may further include moving the debridement head relative to the working surface with the drive system, and positioning the debridement head in contact with the tissue site. The drive system may be operable to impart movement from the impeller to the debridement head.

In other embodiments, a system for debriding tissue from a tissue site may include a debridement tool, a therapy device, and a multi-lumen conduit. The debridement tool may include a housing, a handle, a reduced-pressure lumen, a feedback pressure lumen, a debridement head, an impeller, and a drive system. The housing may include an interior space and a working surface. The working surface may be adapted to face a tissue site and may have a working surface port disposed through the working surface. Further, the working surface may be in fluid communication with the interior space through the working surface port. The handle may be coupled to the housing. The reduced-pressure lumen may be in fluid communication with the working surface port and may be adapted to communicate reduced pressure. Further, the reduced-pressure lumen may be in fluid communication with the interior space through the handle. The feedback pressure lumen may be in fluid communication with the interior space and may be adapted to communicate reduced pressure. Further, the feedback pressure lumen may be in fluid communication with the interior space through the handle. The debridement head may be moveable relative to the housing and may have an exterior surface rotatable about a debridement head axis. The exterior surface of the debridement head may comprise an abrasive portion. Further, the debridement head may be positioned within the interior space, and at least a portion of the exterior surface of the debridement head may be adapted to protrude through the working surface port. The impeller may be moveable relative to the housing and may be positioned in fluid communication with the reduced-pressure lumen. The impeller may include a plurality of impeller vanes rotatable about an impeller axis and may be adapted to rotate by operation of reduced pressure being applied to the impeller vanes. Further, the impeller may be positioned in fluid communication with the interior space. The drive system may be coupled between the impeller and the debridement head. The drive system may include an impeller pulley, a debridement head pulley, and a drive belt. The impeller pulley may be coupled to the impeller and rotatable about the impeller axis. The debridement head pulley may be coupled to the debridement head and rotatable about the debridement head axis. The drive belt may be positioned about the impeller pulley and the debridement head pulley such that the drive system may be configured to impart movement from the impeller to the debridement head.

The therapy device may include a reduced-pressure source, a pressure sensor, and a canister. The reduced-pressure source may be in fluid communication with the impeller and the working surface port. Further, the reduced-pressure source may be in fluid communication with the reduced-pressure lumen through the canister, and the feedback pressure lumen may be in fluid communication with the pressure sensor. The multi-lumen conduit may be coupled in fluid communication between the debridement tool and the therapy device. The multi-lumen conduit may include a primary lumen and a secondary lumen. The primary lumen may be in fluid communication with the reduced-pressure lumen, and the secondary lumen may be in fluid communication with the feedback pressure lumen.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. Thus, the following detailed description is non-limiting with the scope of the illustrative embodiments being defined by the appended claims. As used herein, unless otherwise indicated, the use of "or" does not require mutual exclusivity.

Figure 1:
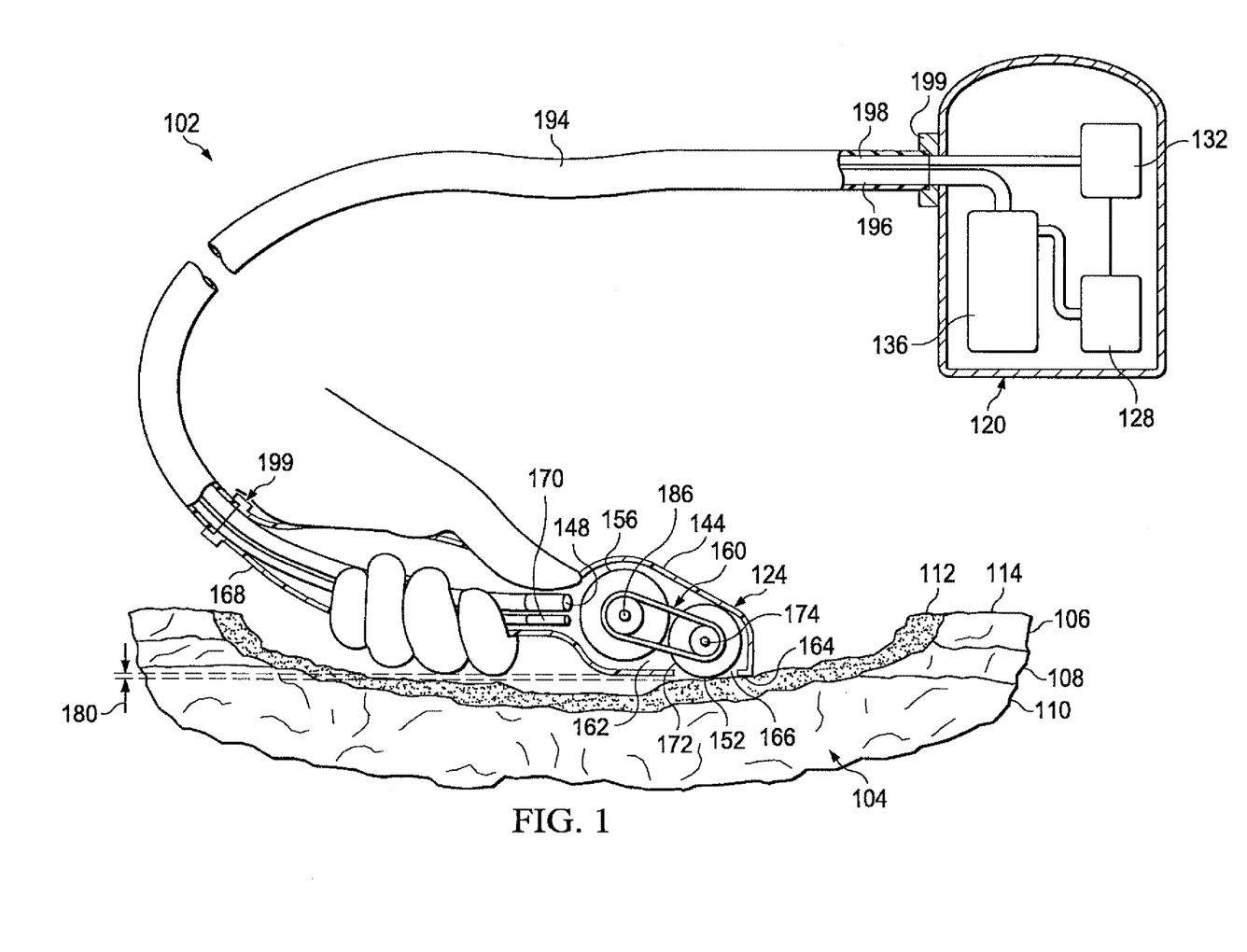
FIG. 1 is a cut-away view of an illustrative embodiment of a system for debriding a tissue site, depicting an illustrative embodiment of a debridement tool deployed at the tissue site.

Referring to the drawings, FIG. 1 depicts an illustrative embodiment of a system 102 for debriding tissue from a tissue site 104 of a patient. The tissue site 104 may extend through or otherwise involve an epidermis 106, a dermis 108, and a subcutaneous tissue 110. The tissue site 104 may be a sub-surface tissue site as depicted in FIG. 1 that extends below the surface of the epidermis 106. Further, the tissue site 104 may be a surface tissue site (not shown) that predominantly resides on the surface of the epidermis 106, such as, for example, an incision. The system 102 may also be utilized without limitation at other tissue sites.

The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Debriding tissue from the tissue site 104 may include the removal of fluids, such as exudate or ascites, and the removal of necrotic tissue 112 from the tissue site 104 in effort to promote the healing of healthy tissue 114.

The terms "debride", "debriding", and "debridement" as used herein may refer to the removal of the necrotic tissue 112 to improve the healing potential of the remaining healthy tissue 114. The term "necrotic tissue" as used herein may refer to dead, damaged, or infected tissue. Although in some embodiments the debridement of necrotic tissue may involve an incision or cut to be made at a tissue site, the disclosed embodiments may also be used to debride necrotic tissue without requiring any such incisions or cuts.

Referring to the illustrative embodiments of FIG. 1, the system 102 may include a therapy device 120 and a debridement tool 124. The therapy device 120 may include a reduced-pressure source 128, a pressure sensor 132, and a canister 136. Components of the system 102 may be omitted, added, or modified as described herein in other embodiments. Further, components of the system 102 may be provided integrally or separate where applicable. For example, the reduced-pressure source 128, the pressure sensor 132, and the canister 136 may be provided integrally as part of the therapy device 120 as shown in FIG. 1, or as separate components.

The reduced-pressure source 128 may provide reduced pressure to the debridement tool 124 and the tissue site 104. In some embodiments, the canister 136 may be in fluid communication between the reduced-pressure source 128 and the debridement tool 124 for collecting fluids and other matter, such as exudate, dislodged necrotic tissue, and waste, from the tissue site 104. For example, reduced pressure may be communicated to the debridement tool 124 through the canister 136, whereby such fluids can be drawn through the debridement tool 124 and communicated to the canister 136 by operation of the reduced pressure being applied. The canister 136 may be any suitable containment device having a sealed internal volume capable of retaining the fluids and other matter described above.

The reduced-pressure source 128 may be any suitable device for providing reduced pressure, such as, for example, a vacuum pump, wall suction, hand pump, or other source. In some embodiments, the reduced-pressure source 128 may be capable of delivering a flow rate between about 5 liters per minute to about 10 liters per minute. In other embodiments, the flow rate may be between about 6 liters per minute to about 8 liters per minute. As an additional example, the reduced-pressure source 128 may be provided as a component of an InfoV.A.C.® therapy unit or a V.A.C. Ulta® therapy unit available from Kinetic Concepts, Inc. of San Antonio, Tex.

As used herein, the term "reduced pressure" may refer to a pressure less than the ambient pressure at a tissue site being treated or debrided. In some embodiments, the reduced pressure may be less than the atmospheric pressure. In some embodiments, the reduced pressure may be less than a hydrostatic pressure at a tissue site. Unless otherwise indicated, values of pressure stated herein are gauge pressures. While the amount and nature of reduced pressure applied to a tissue site may vary according to the application, the reduced pressure may be between about 0 mm Hg to about −500 mm Hg. In some embodiments, the reduced pressure may be between about −75 mm Hg to about −200 mm Hg.

The reduced pressure delivered may be constant, varied, patterned, or random, and may be delivered continuously or intermittently. Although the terms "vacuum" and "negative pressure" may be used to describe the pressure applied to the debridement tool 124 and the tissue site 104, the actual pressure may be more than the pressure normally associated with a complete vacuum. Further, an increase in reduced pressure may correspond to a reduction in pressure (more negative relative to ambient pressure), and a decrease in reduced pressure may correspond to an increase in pressure (less negative relative to ambient pressure).

Referring to FIGS. 1-4, the debridement tool 124 may include a housing 144, a reduced-pressure lumen 148, a debridement head 152, an impeller 156, and a drive system 160. The housing 144 may include an interior space 162 and a working surface 164. The working surface 164 may be adapted to face the tissue site 104, and may have a working surface port 166 disposed through the working surface 164. The working surface 164 may be in fluid communication with the interior space 162 through the working surface port 166. Further, the reduced-pressure source 128 may be in fluid communication with the working surface 164 through the working surface port 166. In some embodiments, a handle 168 may be coupled to the housing 144 to provide a user with an ergonomic grip for the debridement tool 124. Components of the debridement tool 124 may be coupled to or otherwise associated with the housing 144 in any suitable manner consistent with the operational parameters described herein.

The housing 144 of the debridement tool 124 may comprise a medical-grade polymer, metal, or other suitable material. As non-limiting examples, the housing 144 may be formed from polyurethane, polyethylene, polyvinyl chloride (PVC), fluorosilicone, ethylene-propylene, ABS, or similar material. In some illustrative, non-limiting embodiments, the housing 144 may be molded from DEHP-free PVC, ABS or other suitable medical grade polymer. The housing 144 may be formed in any suitable manner such as by molding, casting, machining, or extruding. Further, the housing 144 may be formed as an integral unit or as individual components.

The reduced-pressure lumen 148 may be in fluid communication with the working surface 164 through the working surface port 166 for communicating reduced pressure. In some embodiments, the reduced-pressure lumen 148 may be in fluid communication with the interior space 162 through the handle 168. Further, the reduced-pressure source 128 may be in fluid communication with the reduced-pressure lumen 148 through the canister 136.

In some embodiments, a feedback pressure lumen 170 may be in fluid communication with the interior space 162 of the housing 144. For example, the feedback pressure lumen 170 may be in fluid communication with the interior space 162 through the handle 168. Further, the feedback pressure lumen 170 may be fluidly isolated from the reduced-pressure lumen 148 along the length of the handle 168. In some embodiments, the feedback pressure lumen 170 may be in fluid communication with the pressure sensor 132. For example, the feedback pressure lumen 170 may be adapted to communicate reduced pressure, such as a reduced pressure feedback signal, from the debridement tool 124 and/or the tissue site 104 to the pressure sensor 132. Thus, although in some embodiments the feedback pressure lumen 170 and the reduced-pressure lumen 148 may be in fluid communication with the interior space 162, the feedback pressure lumen 170 and the reduced-pressure lumen 148 may be physically separate from one another.

Figure 2:
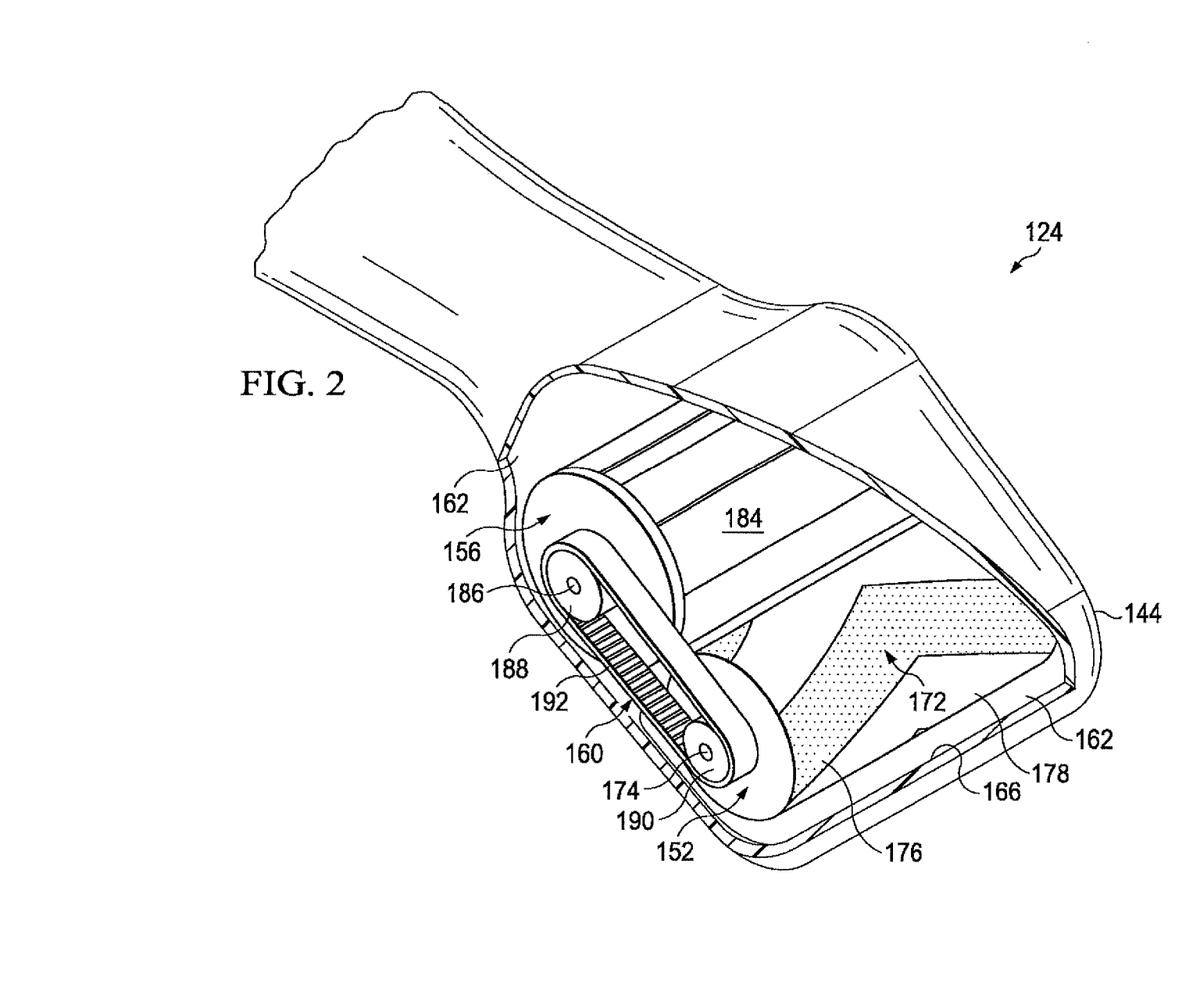
FIG. 2 is a perspective, cut-away view of the debridement tool of FIG. 1.
Figure 3:
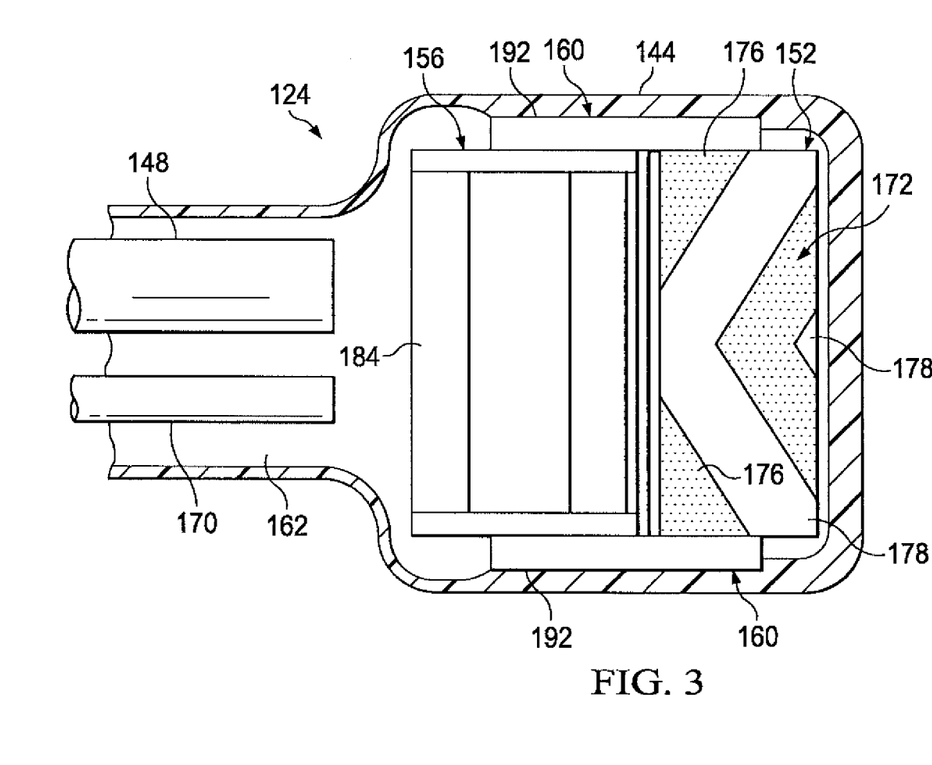
FIG. 3 is a top, cut-away view of the debridement tool of FIG. 1.
Figure 4:
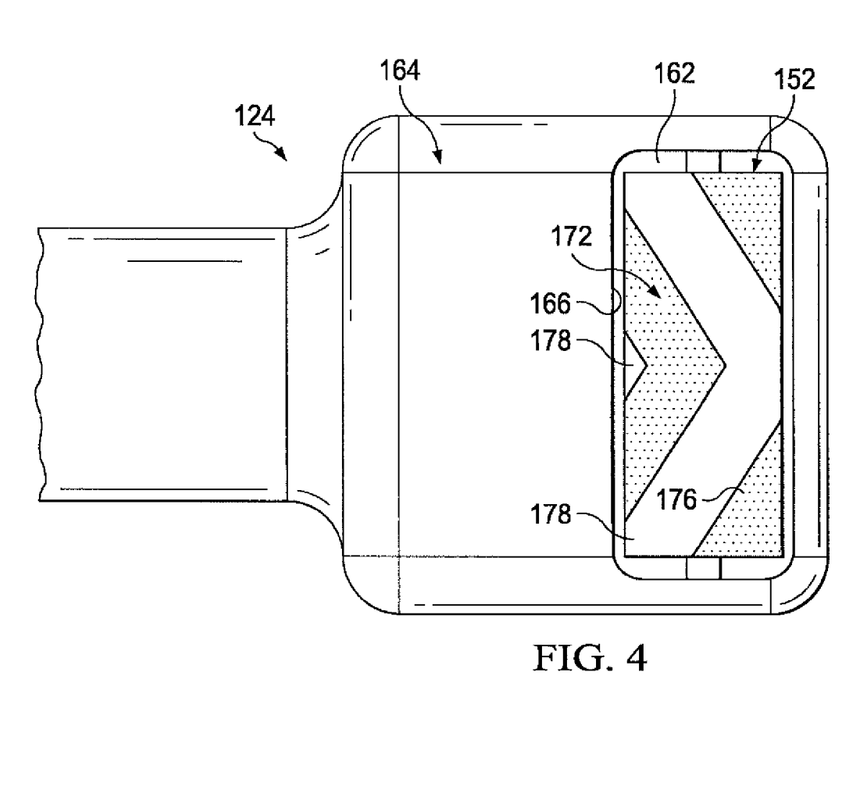
FIG. 4 is a bottom view of the debridement tool of FIG. 1, depicting an illustrative embodiment of a working surface and a working surface port.

The debridement head 152 may be moveable relative to the housing 144 and may be cylindrical in shape. In some embodiments, the debridement head 152 may have an exterior surface 172 rotatable about a debridement head axis 174. As shown in FIGS. 2-4, the exterior surface 172 of the debridement head 152 may comprise an abrasive portion 176. In some embodiments, the exterior surface 172 of the debridement head 152 may comprise the abrasive portion 176 and an optional non-abrasive portion 178. The debridement head 152 may be positioned within the interior space 162, and at least a portion of the exterior surface 172 of the debridement head 152 may be adapted to protrude through the working surface port 166. In some embodiments, the exterior surface 172 of the debridement head 152 may be adapted to protrude through the working surface port 166 and beyond the working surface 164 by a debridement depth 180 between about 0.5 millimeters to about 2.0 millimeters.

Referring to FIGS. 2-3, in some embodiments, the exterior surface 172 of the debridement head 152 may comprise a plurality of the abrasive portions 176 and a plurality of the non-abrasive portions 178. The abrasive portions 176 may be positioned between the non-abrasive portions 178 about a circumference of the exterior surface 172 of the debridement head 152. Such a configuration alternating the abrasive portions 176 and the non-abrasive portions 178 may enhance the ability of the debridement head 152 to rotate in contact with the tissue site 104 without becoming bound against the tissue site 104. The abrasive portions 176 may comprise any suitable abrasive material such as, for example, a coarse grade sandpaper, a coating of grit, crushed media, or similar material. In some embodiments, the abrasive portions 176 may comprise without limitation protruding polymer bristles, metal wire, fibers, or cutting teeth. Further, a variety of interchangeable debridement heads 152 having different combinations of abrasives as described above may be provided in a kit with the debridement tool 124.

Continuing with FIGS. 2-3, the impeller 156 may be moveable relative to the housing 144 and be positioned in fluid communication with the reduced-pressure lumen 148. In some embodiments, the impeller 156 may include a plurality of impeller vanes 184 rotatable about an impeller axis 186. The impeller 156 may be adapted to rotate by operation of reduced pressure being applied to the impeller vanes 184. For example, the impeller 156 may be positioned within the interior space 162 and/or in fluid communication with the interior space 162 in the path of reduced pressure being communicated therethrough. In some embodiments, the reduced-pressure source 128 may be in fluid communication with the impeller 156 through the reduced-pressure lumen 148.

Referring to FIGS. 1-3, the drive system 160 may be coupled to or between the impeller 156 and the debridement head 152. In some embodiments, the drive system 160 may include an impeller pulley 188, a debridement head pulley 190, and a drive belt 192. The impeller pulley 188 may be coupled to the impeller 156 and be rotatable with the impeller 156 about the impeller axis 186. The debridement head pulley 190 may be coupled to the debridement head 152 and be rotatable with the debridement head 152 about the debridement head axis 174. The drive belt 192 may be positioned about the impeller pulley 188 and the debridement head pulley 190 such that the drive system 160 may be configured to impart movement from the impeller 156 to the debridement head 152. Although FIG. 3 depicts the drive system 160 positioned at each opposing end of the debridement head axis 174 and the impeller axis 186, other embodiments may use the drive system 160 at only one end of the debridement head axis 174 and the impeller axis 186. Further, although not explicitly shown in the drawings, the housing 144 may have, for example, brackets, pins, axles, bearings and other such devices for coupling or associating the impeller 156, the debridement head 152, the drive system 160, and other components of the debridement tool 124 with the housing 144 as described herein.

Referring to FIG. 1, the debridement tool 124 may be coupled in fluid communication with the therapy device 120, or individual components of the therapy device 120 set forth above. For example, the reduced-pressure lumen 148 of the debridement tool 124 may be in fluid communication with the reduced-pressure source 128, and the feedback pressure lumen 170 of the debridement tool 124 may be in fluid communication with the pressure sensor 132. In some embodiments, the reduced-pressure source 128 may be in fluid communication with the impeller 156 and the working surface port 166. Further, in some embodiments, the reduced-pressure source 128 may be in fluid communication with the impeller 156 through the reduced-pressure lumen 148. Even further, in some embodiments, the reduced-pressure source 128 may be in fluid communication with the reduced-pressure lumen 148 through the canister 136.

Continuing with FIG. 1, in some embodiments, a multi-lumen conduit 194 may be coupled in fluid communication between the debridement tool 124 and the therapy device 120. The multi-lumen conduit 194 may include multiple lumens, such as a primary lumen 196 and a secondary lumen 198. The reduced-pressure lumen 148 may be coupled in fluid communication with the primary lumen 196 for providing fluid communication with the reduced-pressure source 128. Further, the feedback pressure lumen 170 may be coupled in fluid communication with the secondary lumen 198 for providing fluid communication with the pressure sensor 132. The primary lumen 196 may be substantially isolated from fluid communication with the secondary lumen 198 along the length of the multi-lumen conduit 194. Although shown in FIG. 1 as having a substantially circular cross-section, the multi-lumen conduit 194 may have any shape to suit a particular application. Further, the multi-lumen conduit 194 may comprise, for example, a flexible polymer. Each distal end of the multi-lumen conduit 194 may include a connector 199 for coupling the multi-lumen conduit 194 in fluid communication between the therapy device 120 and the debridement tool 124.

Referring to FIGS. 1-4, in an illustrative embodiment of operation, the working surface 164 of the debridement tool 124 may be positioned proximate to or in contact with the necrotic tissue 112 at the tissue site 104. The external surface 172 of the debridement head 152 may be positioned in contact with the necrotic tissue 112, and the working surface port 166 may be positioned in fluid communication with the tissue site 104. Reduced pressure may be communicated from the reduced-pressure source 128 to the impeller 156 of the debridement tool 124 and to the tissue site 104 through the working surface port 166. Reduced pressure may induce fluid flow across the impeller vanes 184 of the impeller 156 to impart movement or rotation on the impeller 156. Rotation of the impeller 156 and the impeller pulley 188 coupled to the impeller 156 may be operable to impart rotation on the debridement head 152 in a corresponding manner. For example, the drive belt 192 that may be coupled between the impeller pulley 188 and the debridement head pulley 190 may impart rotational movement from the impeller 156 to the debridement head 152. Such movement of the debridement head 152 while being positioned in contact with the necrotic tissue 112 may operate to debride or otherwise dislodge the necrotic tissue 112 from the tissue site 104. A saline or water solution may be added at the tissue site 104 to assist with dislodging the necrotic tissue 112, preventing blockages, and reducing pain for the patient.

Reduced pressure being applied to the tissue site 104 may extract the dislodged necrotic tissue 112, fluids, wound exudate, or other waste material from the tissue site 104 without disturbing the healthy tissue 114 that may surround and/or underlie the necrotic tissue 112. Further, since the external surface 172 of the debridement head 152 may protrude through the working surface port 166, the working surface 166 may operate as a guard or guide for the debridement operation. For example, the working surface 166 may substantially preclude the debridement head 152 from entering or engaging the tissue site 104 at a depth beyond the prescribed debridement depth 180, which may damage or disrupt the healthy tissue 114. In this manner, the debridement tool 124 according to this disclosure may provide enhanced control for the user and safety for the patient, which may also reduce the amount of training required for use of the debridement tool 124. Further, since the debridement tool 124 is mechanical in operation by virtue of reduced pressure incident on the impeller 156, the debridement tool 124 may provide the user with a low cost, disposable option for performing debridement.

Further, the therapy device 120 may be configured to control the amount of reduced pressure from the reduced-pressure source 128 being applied to the debridement tool 124 and the tissue site 104 according to a user input and/or reduced-pressure feedback signal. For example, the reduced-pressure feedback signal may be communicated from the feedback pressure lumen 170 of the debridement tool 124 to the pressure sensor 132. The therapy device 120 and the system 102 may include additional control circuitry, processors, and sensors as necessary for processing and monitoring the reduced pressure being applied to the debridement tool 124 and the tissue site 104. For example, a processor (not shown) including a control algorithm may be associated with the pressure sensor 132 in any suitable manner for controlling the output from the reduced-pressure source 128 according to the reduced-pressure feedback signal and/or user input.

In some embodiments, a feedback reduced pressure less than about −5 mm Hg and decreasing to about 0 mm Hg may be measured at the working surface 164 and/or the tissue site 104 through the feedback pressure lumen 170 in normal operation of the system 102. If the reduced pressure output measured at the reduced-pressure source 128 reaches a maximum reduced pressure, such as between about −300 mm Hg to about −400 mm Hg, while the feedback reduced pressure is less than about −5 mm Hg, or about 0 mm Hg, then a debridement tubing blockage alarm may be reported. The debridement tubing blockage alarm may indicate a blockage in the reduced-pressure lumen 148. In other embodiments, the maximum reduced pressure may be between about −300 mm Hg to about −380 mm Hg.

In some embodiments, if the feedback reduced pressure is between about −5 mm Hg to about −100 mm Hg, then a partial head-blockage alarm may be reported. The partial head-blockage alarm may indicate a partial blockage in the debridement tool 124, such as, for example, at or among the interior space 162 of the housing 144, the debridement head 152, the working surface 164, or the working surface port 166. The partial head-blockage alarm may serve as an alert to the user that the debridement tool 124 requires cleaning or replacement, but the system 102 may otherwise remain operable during a partial head-blockage alarm.

In some embodiments, if the feedback reduced pressure is greater than about −100 mm Hg, then the reduced-pressure source 128 may increase the reduced pressure output to the maximum reduced pressure set forth above for a set time period to remediate the blockage. If the feedback reduced pressure does not decrease or otherwise move toward normal operational levels, such as about 0 mm Hg, after the set time period, then a full head blockage alarm may be reported and the system 102 may shut down.

Based on the above operational and control parameters, the system 102 can detect blockages in the debridement tool 124 that may prevent components of the debridement tool 124 from rotating, such as the debridement head 152. Further, the system 102 may be configured to detect if the debridement tool 124 has become sealed against the tissue site 104, restricting flow and causing an increase in reduced pressure at the tissue site 104. The system 102 may take the steps described above to alert a user and shut down the reduced-pressure source 128 as necessary.

In some illustrative embodiments, a method for debriding the tissue site 104 may include providing the debridement tool 124. In some embodiments, the debridement tool 124 may include the housing 144, the debridement head 152, the impeller 156, and the drive system 160. The housing 144 may include the interior space 162 and the working surface 164. The working surface port 166 may be disposed through the working surface 164 and in fluid communication with the interior space 162. The debridement head 152 may be moveable relative to the housing 144, and the drive system 160 may be coupled between the impeller 156 and the debridement head 152.

The method may further include communicating reduced pressure to the working surface 164 and communicating reduced pressure to the impeller 156. In some embodiments, the reduced pressure may be communicated to the working surface 164 through the working surface port 166. In other embodiments, the reduced pressure may be communicated to the working surface 164 and/or the tissue site 104, for example, by a lumen or conduit (not shown) that may be separate from, integral with, or attached to the debridement tool 124. The impeller 156 may be configured to rotate by operation of reduced pressure being applied to the impeller 156. Further, the method may include moving the debridement head 152 relative to the housing 144 with the drive system 160, and positioning the debridement head 152 in contact with the tissue site 104. In some embodiments, the working surface 164 may be positioned in contact with the tissue site 104 along with the debridement head 152. The drive system 160 may be operable to impart movement from the impeller 156 to the debridement head 152.

In some embodiments, the method may further include dislodging the necrotic tissue 112 from the tissue site 104 by moving the debridement head 152 relative to the tissue site 104 when the debridement head 152 is in contact with the tissue site 104 and reduced pressure is being communicated to the impeller 156. In some embodiments, the method may further include removing dislodged necrotic tissue 112 from the tissue site 104 by operation of reduced pressure being communicated to the working surface 164. In some embodiments, the method may further include communicating dislodged necrotic tissue 112 into the canister 136 by operation of the reduced pressure being applied to the working surface 164.

In some embodiments, the method may further include comparing a reduced pressure output being communicated to the working surface 164 with a feedback reduced pressure measured within the interior space 162 of the housing 144. In some embodiments, the method may further include signaling a debridement tubing blockage alarm if the reduced pressure output is at a maximum reduced pressure and the feedback reduced pressure is substantially zero, or between about 0 mm Hg to about −5 mm Hg. In some embodiments, the method may further include signaling a partial head-blockage alarm if the feedback reduced pressure is between about −5 mm Hg to about −100 mm Hg.

In some embodiments, the method may further include: increasing the reduced pressure output to a maximum pressure for a set time period if the feedback reduced pressure is greater than −100 mm Hg; signaling a full head blockage alarm if the feedback reduced pressure is greater than −100 mm Hg after the set time period; and shutting off the reduced pressure output if the feedback reduced pressure is greater than −100 mm Hg after the set time period.

Although this specification discloses advantages in the context of certain illustrative, non-limiting embodiments, various changes, substitutions, permutations, and alterations may be made without departing from the scope of the appended claims. Further, any feature described in connection with any one embodiment may also be applicable to any other embodiment.

What is claimed is:

1. A system for debriding tissue from a tissue site, comprising:
    a debridement tool, comprising:
        a housing comprising an interior space,
        a reduced-pressure lumen adapted to communicate reduced pressure,
        a debridement head moveable relative to the housing and positioned within the interior space,
        an impeller moveable relative to the housing and positioned within the interior space in fluid communication with the reduced-pressure lumen and the debridement head, and
        a drive system coupled between the impeller and the debridement head, the drive system being configured to impart movement from the impeller to the debridement head;
    a therapy device, comprising:
        a reduced-pressure source in fluid communication with the impeller through the reduced-pressure lumen,
        a pressure sensor, and
        a canister configured to retain fluid from the tissue site drawn through the debridement tool; and
    a multi-lumen conduit comprising a primary lumen and a secondary lumen in fluid communication between the debridement tool and the therapy device, the primary lumen in fluid communication with the reduced-pressure lumen and the secondary lumen in fluid communication between the interior space and the pressure sensor.

2. The system of claim 1, further comprising a working surface adapted to face the tissue site, and a working surface port disposed through the working surface.

3. The system of claim 2, wherein the working surface is in fluid communication with the interior space through the working surface port.

4. The system of claim 2, wherein the reduced-pressure lumen is in fluid communication with the working surface through the working surface port.

5. The system of claim 2, wherein the reduced-pressure source is in fluid communication with the working surface through the working surface port.

6. The system of claim 1, wherein the reduced-pressure lumen is in fluid communication with the interior space.

7. The system of claim 1, further comprising a handle coupled to the housing, wherein the reduced-pressure lumen is in fluid communication with the interior space through the handle.

8. The system of claim 1, further comprising a feedback pressure lumen adapted to communicate reduced pressure between the secondary lumen and the interior space.

9. The system of claim 8, wherein the pressure sensor is in fluid communication with the feedback pressure lumen.

10. The system of claim 8, further comprising a handle coupled to the housing, wherein the feedback pressure lumen is in fluid communication with the interior space through the handle.

11. The system of claim 1, wherein the debridement head comprises a debridement head axis and an exterior surface rotatable about the debridement head axis, the exterior surface of the debridement head comprising an abrasive portion.

12. The system of claim 11, wherein the exterior surface of the debridement head is cylindrical.

13. The system of claim 11, wherein the exterior surface of the debridement head further comprises a non-abrasive portion.

14. The system of claim 11, wherein the abrasive portion is a plurality of abrasive portions, the exterior surface of the debridement head further comprising a plurality of non-abrasive portions, the abrasive portions being positioned between the non-abrasive portions about the exterior surface of the debridement head.

15. The system of claim 11, wherein the abrasive portion is selected from a group consisting of: a coating of grit; protruding bristles; and protruding wires.

16. The system of claim 11, wherein the abrasive portion comprises at least one cutting tooth.

17. The system of claim 11, wherein the housing further comprises a working surface adapted to face the tissue site, and a working surface port disposed through the working surface, at least a portion of the exterior surface of the debridement head being adapted to protrude through the working surface port.

18. The system of claim 17, wherein the exterior surface of the debridement head is adapted to protrude through the working surface port and beyond the working surface between about 0.5 millimeters to about 2.0 millimeters.

19. The system of claim 1, wherein the impeller comprises an impeller axis and a plurality of impeller vanes rotatable about the impeller axis.

20. The system of claim 19, wherein the impeller is adapted to rotate by operation of reduced pressure being applied to the impeller vanes.

21. The system of claim 1, wherein the impeller is positioned in fluid communication with the interior space.

22. The system of claim 1, wherein the drive system comprises an impeller pulley, a debridement head pulley, and a drive belt, the impeller pulley being coupled to the impeller and moveable with the impeller, the debridement head pulley being coupled to the debridement head and moveable with the debridement head, the drive belt being positioned about the impeller pulley and the debridement head pulley.

23. The system of claim 1, wherein the reduced-pressure source is in fluid communication with the reduced-pressure lumen through the canister.

24. A system for debriding tissue from a tissue site, comprising:
    a debridement tool, comprising:
        a housing comprising an interior space and a working surface, the working surface adapted to face a tissue site and having a working surface port disposed through the working surface, the working surface being in fluid communication with the interior space through the working surface port, a handle coupled to the housing, a reduced-pressure lumen in fluid communication with the working surface port, the reduced-pressure lumen being adapted to communicate reduced pressure, the reduced-pressure lumen being in fluid communication with the interior space through the handle, a feedback pressure lumen in fluid communication with the interior space, the feedback pressure lumen being adapted to communicate reduced pressure, the feedback pressure lumen being in fluid communication with the interior space through the handle, a debridement head moveable relative to the housing, the debridement head having an exterior surface rotatable about a debridement head axis, the exterior surface of the debridement head comprising an abrasive portion, the debridement head being positioned within the interior space and at least a portion of the exterior surface of the debridement head being adapted to protrude through the working surface port, an impeller moveable relative to the housing and positioned in fluid communication with the reduced-pressure lumen and the debridement head, the impeller comprising a plurality of impeller vanes rotatable about an impeller axis, the impeller adapted to rotate by operation of reduced pressure being applied to the impeller vanes, the impeller being positioned within the interior space, and a drive system coupled between the impeller and the debridement head, the drive system comprising an impeller pulley, a debridement head pulley, and a drive belt, the impeller pulley coupled to the impeller and rotatable about the impeller axis, the debridement head pulley coupled to the debridement head and rotatable about the debridement head axis, the drive belt being positioned about the impeller pulley and the debridement head pulley, the drive system being configured to impart movement from the impeller to the debridement head;

a therapy device comprising a reduced-pressure source, a pressure sensor, and a canister, the reduced-pressure source being in fluid communication with the impeller and the working surface port, the reduced-pressure source being in fluid communication with the reduced-pressure lumen through the canister, the feedback pressure lumen being in fluid communication with the pressure sensor; and a multi-lumen conduit coupled in fluid communication between the debridement tool and the therapy device, the multi-lumen conduit comprising a primary lumen and a secondary lumen, the primary lumen in fluid communication with the reduced-pressure lumen and the secondary lumen in fluid communication with the feedback pressure lumen.

* * * * *